United States Patent
Stenberg et al.

(10) Patent No.: US 10,945,875 B2
(45) Date of Patent: Mar. 16, 2021

(54) DEVICE FOR TREATMENT OF SLEEP APNEA OR SNORING

(71) Applicant: Dental Device Sweden AB, Ljungby (SE)

(72) Inventors: Ulf Stenberg, Ljungby (SE); Anders Karlsson, Ljungby (SE); Antoine Elkhoury, Ljungby (SE)

(73) Assignee: DENTAL DEVICE SWEDEN AB, Ljungby (SE)

( * ) Notice: Subject to any disclaimer, the term of this patent is extended or adjusted under 35 U.S.C. 154(b) by 687 days.

(21) Appl. No.: 14/574,525

(22) Filed: Dec. 18, 2014

(65) Prior Publication Data
US 2015/0182374 A1 Jul. 2, 2015

Related U.S. Application Data

(63) Continuation of application No. PCT/SE2013/050709, filed on Jun. 17, 2013.

(30) Foreign Application Priority Data

Jun. 19, 2012 (SE) .................................. 1250658-0

(51) Int. Cl.
*A61F 5/56* (2006.01)
*A61C 7/36* (2006.01)
*A61C 7/08* (2006.01)

(52) U.S. Cl.
CPC ................ *A61F 5/566* (2013.01); *A61C 7/08* (2013.01); *A61C 7/36* (2013.01)

(58) Field of Classification Search
CPC .... A61F 5/566; A61F 5/56; A61F 5/50; A61F 5/58; A61C 7/08; A61C 5/14; A63B 71/085; A63B 2071/088; A63B 2208/12; A63B 2071/086; A61B 13/00
See application file for complete search history.

(56) References Cited

U.S. PATENT DOCUMENTS

| 5,829,441 A | 11/1998 | Kidd et al. |
| 6,604,527 B1* | 8/2003 | Palmisano ............... A61C 7/08 128/848 |
| 7,520,281 B1 | 4/2009 | Nahabedian |

(Continued)

FOREIGN PATENT DOCUMENTS

| EP | 1698299 A1 | 9/2006 |
| EP | 1094761 B1 | 10/2008 |

(Continued)

OTHER PUBLICATIONS

PCT International Search Report, dated Oct. 4, 2013.

*Primary Examiner* — Ophelia A Hawthorne
(74) *Attorney, Agent, or Firm* — Gabriela B. Tomescu, Esq.; Bergenstrahle & Partners AB

(57) ABSTRACT

A device for treatment of sleep apnea or snoring of a user which has an upper oral splint adapted for an upper jaw of the user, and a lower oral splint adapted for a lower jaw of the user. At least one of the oral splints has adjustment devices on them, with a fixation device for adjustable and detachable fixation of an abutment element. Since the abutment elements are adjustable and detachable, a flexible device is provided where the setting can be adjusted and parts can be replaced when needed.

17 Claims, 5 Drawing Sheets

(56) References Cited

U.S. PATENT DOCUMENTS

| | | | |
|---|---|---|---|
| 8,156,940 B2* | 4/2012 | Lee | A61F 5/566 |
| | | | 128/848 |
| 8,316,857 B2 | 11/2012 | Thornton | |
| 8,517,029 B2* | 8/2013 | Nelissen | A61F 5/566 |
| | | | 128/848 |
| 2011/0017220 A1* | 1/2011 | Lindsay | A61F 5/566 |
| | | | 128/848 |
| 2011/0168187 A1 | 7/2011 | Nelissen | |
| 2012/0227750 A1* | 9/2012 | Tucker | A61F 5/566 |
| | | | 128/848 |

FOREIGN PATENT DOCUMENTS

| | | |
|---|---|---|
| JP | H09503706 A | 4/1997 |
| JP | 2002519137 A | 7/2002 |
| JP | 2010509980 A | 4/2010 |
| WO | 1996020810 A1 | 7/1996 |
| WO | 2000001317 A1 | 1/2000 |
| WO | 2007137302 A2 | 11/2007 |
| WO | 2008060122 A1 | 5/2008 |
| WO | 2011063180 A1 | 5/2011 |
| WO | 2011146419 A1 | 11/2011 |

* cited by examiner

DEVICE FOR TREATMENT OF SLEEP APNEA OR SNORING

This application is a continuation of PCT/SE2013/050709, filed Jun. 17, 2013 which claims priority to SE 1250658-0, filed on Jun. 19, 2012, the entire contents of each of which are hereby incorporated by reference.

BACKGROUND

The present invention relates generally to a device for treatment of sleep apnea.

Snoring is a disturbing behaviour, which is more common among men than women and the tendency to snore increases with age. A snoring person can wake up several times every night or period of sleep which results in tiredness and decreased ability to concentrate for the person concerned. In worst case the chronic tiredness can lead to more or less serious depressions.

Apnea is a disease which means that the tongue and the lower jaw slide backward towards the throat and obstruct or even block breathing, which medically affects the person. If such a blocking occurs, the person often wakes up. One such consequence with disturbances in the respiratory process during sleep is impaired ventilation. This in turn affects the person negatively in that the natural gas exchange is lower, and the oxygen supply to the different organs, particularly the brain, becomes too low. The level of carbon dioxide in the blood is also elevated. Disturbances of this kind lead in serious cases to so-called obstructive sleep apnea syndrome (OSAS).

In order to avoid these conditions, so-called oral splints are used to maintain the lower jaw in a forward position during sleep. The respiratory tract is thereby kept open which counteracts respiratory arrest as well as snoring.

Due to the reasons given above different appliances have been designed to prevent the backward movement of the tongue.

WO2011/063180 describes a device for treatment of sleep apnea which comprises a first body for use in the upper jaw and a second body which can be fitted to the upper body for use in the lower jaw. The first body comprises a first element and the second body comprises a second element. The first element slidingly connects the second element and the second body has a wall which slides along a wall of the first body which displaces the second body. The second body is secured to at least a dental implant in the lower jaw.

Today's devices are interconnected which leads to several disadvantages. One of the disadvantages is the inability to open the mouth or talk intelligibly when the device is placed in the mouth, which, besides the inconvenience, also can cause claustrophobic feelings of the user. Another disadvantage is that you have to disassemble the entire device if adjustments between the upper and lower bodies of the device are needed. This is very costly for society and the user since every device is customised and handmade and must then be replaced by a new part. These are some of the reasons why there is a need for devices with are user friendly and cost efficient.

SUMMARY OF INVENTION

An object of the present invention is to remove some of the problems associated with today's devices.

According to a first aspect of the invention there is provided a device for treatment of apnea or snoring of a user, comprising a first oral splint adapted for an upper jaw of the user, wherein the first oral splint comprises two upper abutment elements, and a second oral splint adapted for a lower jaw of the user, wherein the second oral splint comprises two lower abutment elements, wherein each of the lower abutment elements is adapted to cooperate with a respective one of the two upper abutment elements to bring the second oral splint forward relatively to the first oral sprint during closing of the mouth of the user, wherein at least one of the first and second oral splints comprises adjustment devices for adjusting the positions of the abutment elements, characterized in that the each of the adjustment devices comprises a fixation element for adjustable and detachable fixation of an abutment element. A flexible and cost-efficient device is thereby provided, wherein the adjustment device can be provided separately and the abutment elements can be replaced, without having to replace the entire device.

In a preferred embodiment, the upper and lower oral splints are curved and essentially U-shaped with two legs, one adapted for the left side of the upper and lower jaw, respectively, and one adapted for the right side of the upper and lower jaw, respectively, and wherein four abutment elements are provided, one on each leg of the upper and lower oral splint, respectively. This provides a reliable function of the device.

According to a second aspect of the invention there is provided an adjustment device adapted to be attached to an oral splint adapted for a jaw of a user, characterized by a fixation element for adjustable and detachable fixation of an abutment element, wherein the abutment element is adapted to cooperate with another abutment element to bring an oral splint in the lower jaw of the user forward relatively to an oral sprint in the upper jaw of the user during closing of the mouth of the user.

According to a third aspect of the invention there is provided an abutment element adapted for adjustable and detachable fixation to an adjustment device according to the invention.

Preferred embodiments are defined in the dependent claims.

BRIEF DESCRIPTION OF DRAWINGS

The invention is now described, by way of example, with reference to the accompanying drawings, in which.

DESCRIPTION OF EMBODIMENTS

Before describing the invention in detail it should be appreciated that the invention is not limited to the specific materials or configurations described herein, since these configurations and materials can vary.

It should also be appreciated that the terminology used herein is used merely to describe different embodiments and is not intended to limit the scope of the present invention which is limited only by the appended claims.

The term adjustment device with is used in this text covers the parts which are mounted to adjust the mutual positions of the oral splints, wherein these parts are abutment elements (block), attachments means and fixation elements.

In the following, the invention will be described with reference to the appended drawings, in which different embodiments are shown.

Figure 1:
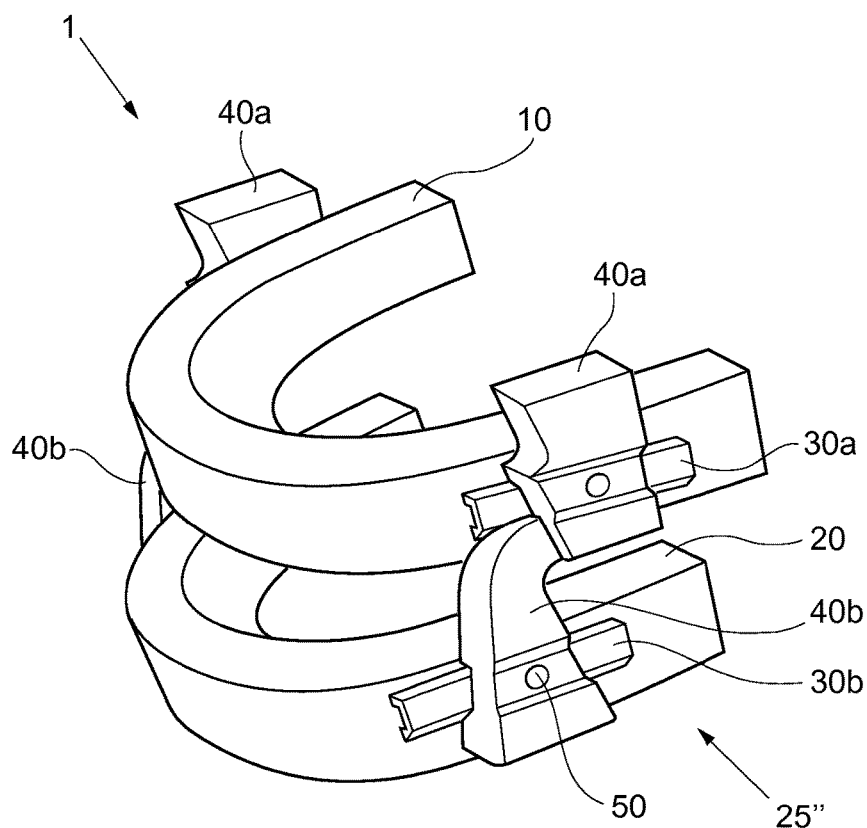
FIG. 1 is a perspective view of a first embodiment of a device for treatment of sleep apnea or snoring according to the present invention.

FIG. 1 shows a perspective view of a first embodiment of a device for treatment of sleep apnea or snoring according to the present invention. The device 1 comprises an upper oral splint 10 and a lower oral splint 20, which cooperate by means of respective abutment elements 40a, 40b. The oral splints comprise adjustment devices 25 for adjusting the positions of the abutment elements. The adjustment devices in turn comprise attachment elements 30 and fixation elements 50. The attachment elements 30 are attached to a respective oral splint 10, 20. The abutment elements 40 are locked in a specified position by means of the fixation elements 50 to a respective attachment element 30.

The abutment elements 40 cooperate so that the abutment elements 40 in the lower oral splint act as a stop for the upper oral splint which then cannot move forward. In other words, when a user of the oral splints closes his or her mouth, then the lower oral splint 20 is brought forward relatively to the upper oral splint 10.

Figure 1A:
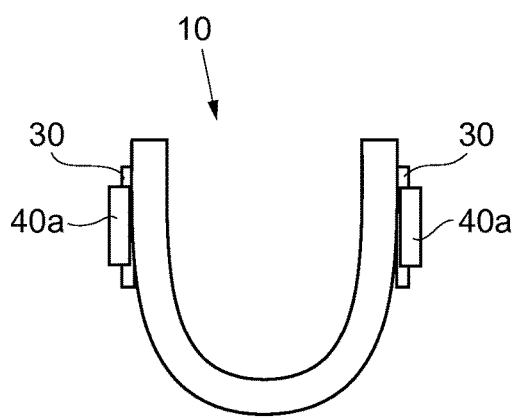
FIG. 1a is a top view of an upper oral splint shown in FIG. 1.

FIG. 1a is a top view of the upper oral splint 10 wherein the positions of the attachment elements 30 and the abutment elements 40a are shown. The upper oral splint 10 is curved and essentially U-shaped with two legs, one adapted for the left side of the upper jaw and one adapted for the right side of the upper jaw. There are provided two abutment elements 40a, one on each leg of the upper oral splint.

Figure 1B:
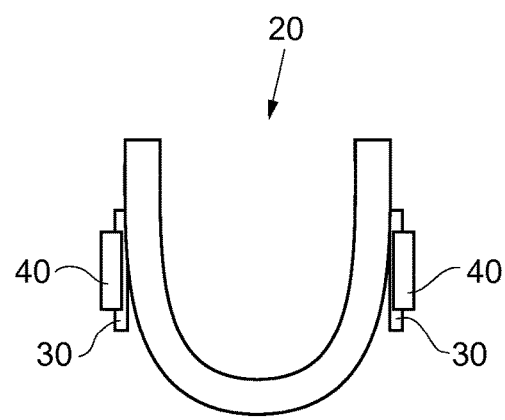
FIG. 1b is a top view of a lower oral splint shown in FIG. 1, FIGS. 2a-c show an embodiment of an attachment element comprised in an adjustment device.

FIG. 1b is a top view of the lower oral splint 20 wherein the positions of the attachment elements 30 and the abutment elements 40b are shown. The lower oral splint 20 is curved and essentially U-shaped with two legs, one adapted for the left side of the lower jaw and one adapted for the right side of the lower jaw. There are provided two abutment elements 40b, one on each leg of the lower oral splint. The positions of the abutment elements 40b of the lower oral splint are slightly forward of the positions of the abutment elements 40a of the upper oral splint so that the lower oral splint 20 is brought forward relatively to the upper oral splint 10 when a user closes his or her mouth.

The abutment elements 40a, 40b can easily be replaced without a major operation in the device. The parts comprised in the adjustment device 25 have different shapes depending on the embodiment and the function of the respective part 30, 40, 50. The fixation element 50 may be a screw, a bolt and/or a nut, an adhesive and/or other chemical fixation element.

The parts comprised in the adjustment devices 25 may be used for both the upper and the lower oral splint and can also be used on either side thereof.

The oral splints 10, 20 are mainly moulded in an acrylic material, although other bio-compatible materials can also be used.

The attachment elements 30 is in this embodiment made of titan but can also be made in other known and suitable materials, such as other metals or acrylic.

The abutment elements 40a, 40b are in this embodiment made of titan but can also be made in other known and suitable materials, such as other metals or acrylic.

Figure 2B:
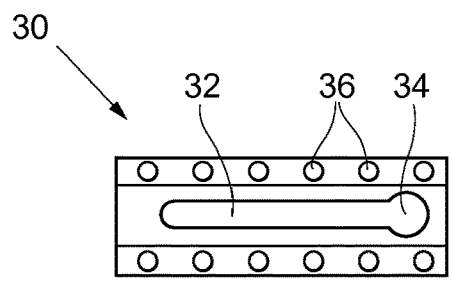
Figure 2C:
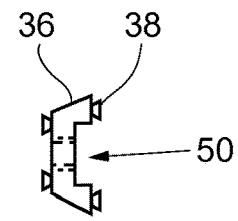
Figure 2A:
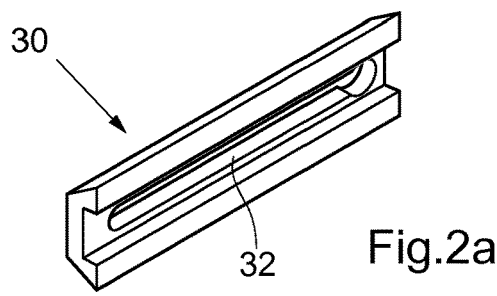

FIGS. 2a-c show an attachment element 30 which is comprised in the adjustment device 25 shown in FIG. 1. FIG. 2a show a perspective view of the attachment element 30, wherein an elongate attachment groove 32 runs in parallel with the length of the attachment element. The attachment groove 32 exhibits in one end an enlarged attachment hole 34 to receive a fixation element 50. The outer longitudinal surface is an engagement surface 36 which the abutment element 40 engages. The length of the attachment element 30 can also be adapted. FIG. 2b shows a front view of the attachment element 30 with the attachment groove 32, the attachment hole 34, and an embedment fixation and retention surfaces 38 for improving the strength by which the attachment element is attached to the oral splint. FIG. 2c shows a side view of the attachment elements 30 wherein the engagement surface 36 is slightly slanting, embedment fixations are provided on both sides of the engagement surface and there is also a space for the fixation element 50.

Figure 3:
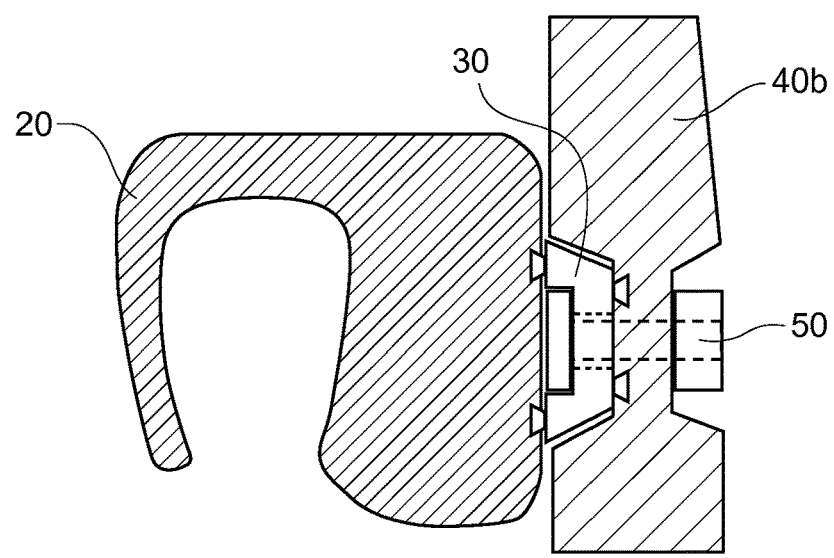
FIG. 3 shows a cross-sectional view of an attachment elements mounted to an oral splint.

FIG. 3 shows a cross-sectional view of a lower oral splint 20 with a mounted adjustment device comprising an attachment element 30, a lower abutment element 40b and a fixation element 50. The abutment element 40b engages the attachment element 30 and the position is fixed by means of the fixation element 50, such as a screw. The abutment element 40b is attached to the attachment element 30 by moving the fixation element 50, such as the head of a screw with a nut mounted thereon, through the attachment hole 34 and the fixation element is thereafter displaced to a desired position in the attachment groove 32, whereafter the nut is tightened. With this design the abutment element can be fixed in a desired position in the attachment element. This position may be adjusted afterward by releasing the nut, displacing the abutment element and subsequently again tightening the nut.

Figure 4B:
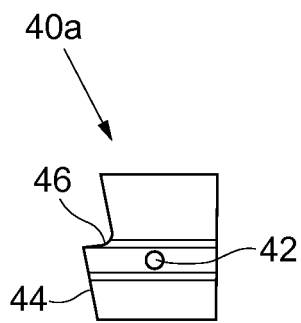
FIGS. 4a-c show different views of a first embodiment of an abutment element.
Figure 4C:
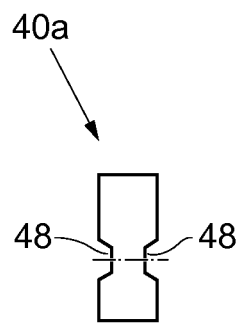
Figure 4A:
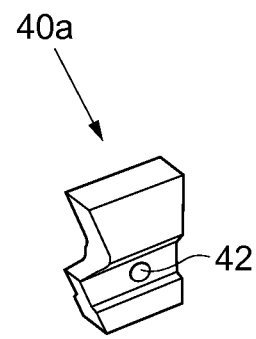

FIGS. 4a-c show an embodiment of an upper abutment element 40a which is comprised in the first embodiment 1 and has the shape of a block. The abutment element engages one of the upper attachment elements 30, see FIG. 1. FIG. 4a shows the lower abutment element 40b in perspective, with an attachment hole 42 where the fixation element 50 is inserted and fixates the lower abutment element 40b in a chosen position. FIG. 4b shows the lower abutment element 40b, wherein the attachment hole 42 is centred and a sliding surface 44 abuts the lower abutment element 40. FIG. 4c shows a side view of the lower abutment element 40b wherein 46 denotes a locking surface which locks the adjustment device in a certain position, the guide groove 48 engages the attachment elements 30.

Figure 5A:
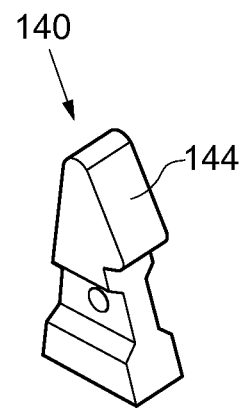
FIGS. 5a-c show different views of a second embodiment of an abutment element.
Figure 5B:
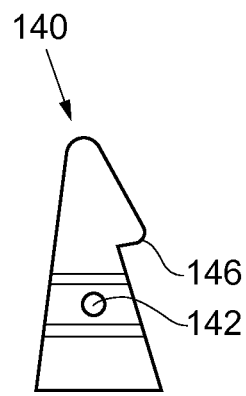
Figure 5C:
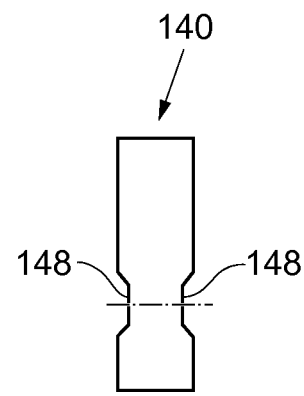

FIGS. 5a-c show an alternative abutment element 140 which in this embodiment is mounted to one of the attachment elements of the lower oral splint. The abutment element 140 is also in the form of a block but is shaped like a fin, see FIG. 5b. FIG. 5a shows a perspective view of the abutment element 140 with a centred attachment hole 142, a hook 144 with a locking surface 146, a slide surface 148 engaging the attachment elements. The locking surfaces 46, see FIG. 4b, and 146 from the upper and lower block, respectively, cooperate and lock the jaws in a determined relationship to each other during sleep. In other words, the locking surface 146 functions in such a way, that it engages the locking surface 146 of the cooperating abutment element and thereby prevents the two oral splints 10, 20 from disengaging from each other and the mouth of the user thereby opens. FIG. 5c shows slide grooves or recesses 148 for right and left mounting. Thus, by making the design of the abutment element symmetrical, the number of different parts is minimized.

Figure 6C:
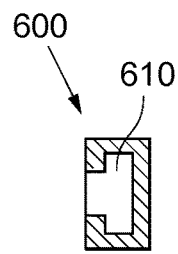
FIGS. 6a-c show detailed views of an attachment element in the form of an attachment rail, FIG. 7 show a cross-sectional view of a second embodiment of an oral splint comprising the attachment rail shown in FIGS. 6a-c, FIGS. 8a-c show views of a further embodiment of an abutment element.
Figure 6B:
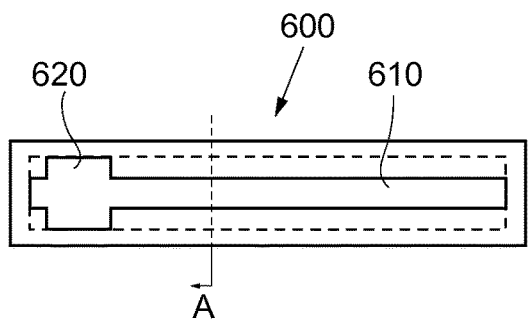
Figure 6A:
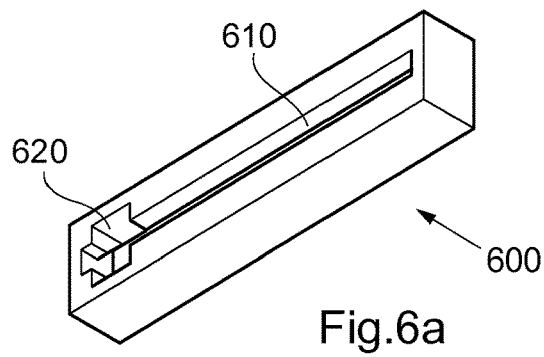

FIGS. 6a-c show a detailed view of a further embodiment of an attachment element in the form of an attachment rail. FIG. 6a shows the attachment rail 600 in a perspective view wherein a groove 610 has an enlarged opening 620 in one end of the groove 610 which receives the abutment element (see slide means or portions 248 and 348 in FIGS. 8 and 9, respectively) which slidingly engages the groove 610. The abutment element is fixated in a determined position by means of a fixation element. FIG. 6b shows the same attachment rail 600 straight from the front wherein the dashed lines show the inner size of the groove where the slide means on the abutment element slidingly engages. FIG. 6c shows a side sectional view of the attachment rail 600 so that the groove 610 with T-shaped cross-sectional shape in which a protruding slide portion with T-shaped cross-sectional shape (see FIGS. 8 and 9) on the abutment element is slidingly received.

Figure 7:
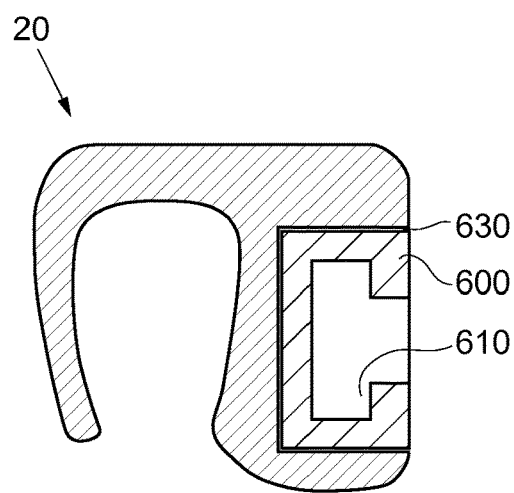

FIG. 7 shows a cross-sectional view of a second embodiment of an oral splint 20, comprising an attachment rail 600 shown in FIGS. 6a-c. The attachment rail 600 comprises a slide groove 610 which slidingly receives the slide portion on an abutment element. The attachment rail 600 also comprises a coating 630 of a retention material, which decreases the movement and increases the friction between the oral splint 20 and the attachment rail 600.

Figure 8B:
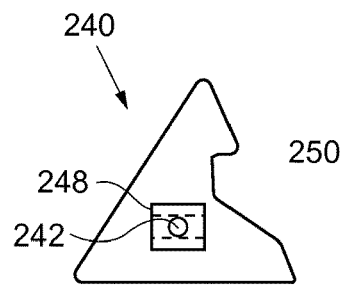
Figure 8C:
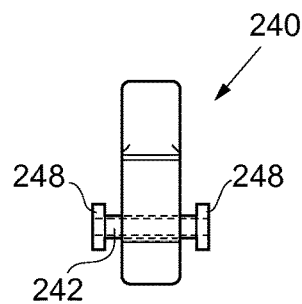
Figure 8A:
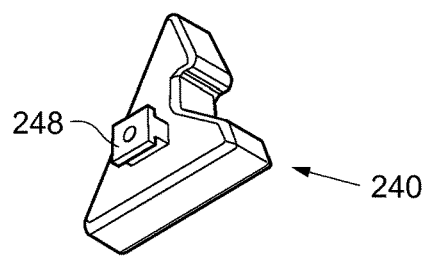

FIG. 8 shows another embodiment of an abutment element 240 with the shape of a fin. FIG. 8a is a perspective view showing a variant of slide means or portion 248 which is inserted into the slide groove in the attachment elements. The upper portion of the abutment element is shaped like a fin, wherein one side is straight but slanting and the other side of the abutment element has a different shape wherein the upper side of the fin exhibits a hook 250, which cooperates with another abutment element in order to fixate a position. The lower portion of the abutment element is broader than the upper portion thereof which is shaped like a fin. FIG. 8b shows a front view of the abutment element where the attachment hole 242 is centred in the slide portion 248. The slide portion 248 is T-shaped in order to be slidingly received in the slide groove 610 of the attachment element, see FIGS. 6a-c. FIG. 8c shows the same abutment element 240 from the side wherein mirroring of the slide portion 248 is shown, so that the parts are adapted for both the left side and the right side of the oral splint.

Figure 9B:
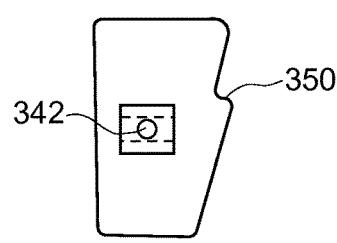
FIGS. 9a-c show different views of a further embodiment of an abutment element.
Figure 9C:
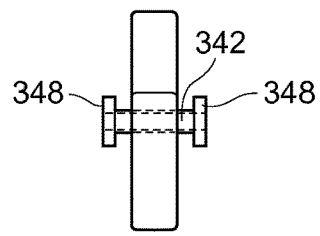
Figure 9A:
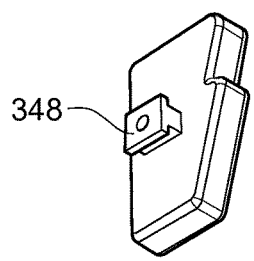

FIG. 9 shows another embodiment of an abutment element 340 in the form of a block, which is comprised in an adjustment device. FIG. 9a is a perspective view of the abutment element 340 which shows a different variant of slide portion 348 which engages the slide groove of the attachment elements and which is fixated by means of fixation element such as a screw (not shown) in the attachment hole. FIG. 9b shows a front view of the abutment element 340 wherein the attachment hole 342 is centred in the slide means. The upper portion of the abutment element is wider than the lower portion thereof, but the means is the widest in the middle portion where a hook 350 is provided. The surfaces cooperate in the same way as described above.

FIG. 9c shows the same attachment element 40 from the side where mirroring of the T-shaped slide means 348 is shown.

Other features and uses of the invention and advantages associated therewith are apparent for the person skilled in the art when reading the description and the different examples.

It will be appreciated that the described embodiment can be varied regarding dimensions without departing from the inventive idea.

The invention claimed is:

1. A device for treatment of sleep apnea or snoring of a user, comprising:
   a first oral splint adapted for an upper jaw of the user, wherein the first oral splint comprises two upper abutment elements disposed on an external lateral side of the first splint, and
   a second oral splint adapted for a lower jaw of the user, wherein the second oral splint comprises two lower abutment elements, disposed on an external lateral side of the second splint, wherein each of the lower abutment elements is adapted to cooperate with a respective one of the two upper abutment elements to bring the second oral splint forward relatively to the first oral sprint during closing of the mouth of the user,
   wherein both the first and second oral splints comprises adjustment devices for adjusting the positions of the abutment elements,
   wherein each of the adjustment devices comprises a fixation element for adjustable and detachable fixation of an abutment element to the respective oral splint.

2. The device according to claim 1, wherein each of the adjustment devices comprises an attachment element adapted to receive the fixation element.

3. The device according to claim 2, wherein each of the attachment elements exhibits a groove.

4. The device according to claim 3, wherein the groove exhibits an enlarged attachment hole, preferably in one end of the groove, to receive a fixation element.

5. The device according to claim 2, wherein each of the abutment elements is provided with a protruding slide portion adapted to be slidingly received in the groove in the attachment element.

6. The device according to claim 5, wherein the groove has T-shaped cross-sectional shape and the protruding slide portion has T-shaped cross-sectional shape.

7. The device according to claim 2, wherein an outer longitudinal surface of each of the attachment elements, preferably a slightly slanting surface, is adapted to engage an abutment element.

8. The device according to claim 1, wherein each of the upper abutment elements is provided with a slanting side adapted to cooperate with a slanting side of a respective lower abutment element.

9. The device according to claim 8, wherein the abutment elements are fin shaped.

10. The device according to claim 1, wherein the upper and lower oral splints are curved and essentially U-shaped with two legs, one adapted for the left side of the upper and lower jaw, respectively, and one adapted for the right side of the upper and lower jaw, respectively, and wherein four abutment elements are provided, one on each leg of the upper and lower oral splint, respectively.

11. The device according to claim 1, wherein the positions of the abutment elements of the lower oral splint are slightly forward of the positions of the abutment elements of the upper oral splint.

12. The device according to claim 1, wherein the fixation element is one of the following: a screw, a bolt, a bolt and a nut, an adhesive and another chemical fixation element.

13. The device according to claim 1, wherein each of the abutment elements is provided with an attachment hole adapted to receive a fixation element for fixation of the abutment element in a chosen position.

14. The device according to claim 1, wherein the abutment elements are symmetrical in shape.

15. The device according to claim 1, wherein each of the upper abutment elements exhibits a hook adapted to engage a hook of a cooperating lower abutment element.

16. An adjustment device adapted to be attached to a device according to claim 1, the adjustment device comprising a fixation element for adjustable and detachable fixation of an abutment element, wherein the abutment element is adapted to cooperate with another abutment element to bring an oral splint in the lower jaw of the user forward relatively to an oral sprint in the upper jaw of the user during closing of the mouth of the user.

17. An abutment element adapted for adjustable and detachable fixation to an adjustment device according to claim 16.

\* \* \* \* \*